US006514458B1

(12) United States Patent
Czechowski et al.

(10) Patent No.: US 6,514,458 B1
(45) Date of Patent: Feb. 4, 2003

(54) METHOD FOR REMOVING MICROBES FROM SURFACES

(75) Inventors: Melvin H. Czechowski, Doylestown, PA (US); Wilson K. Whitekettle, Jamison, PA (US)

(73) Assignee: GE Betz, Inc., Trevose, PA (US)

( * ) Notice: Subject to any disclaimer, the term of this patent is extended or adjusted under 35 U.S.C. 154(b) by 0 days.

(21) Appl. No.: 09/513,770

(22) Filed: Feb. 25, 2000

(51) Int. Cl.$^7$ .............. A61L 9/00; C02F 1/00; C02F 1/68; C02F 5/08; C23G 1/02

(52) U.S. Cl. ............ 422/28; 422/32; 422/37; 210/698; 210/764; 510/247; 510/421; 510/427; 134/3; 134/22.11; 134/22.14; 134/22.19; 134/36; 134/41

(58) Field of Search ........... 422/1, 6–7, 12–19, 422/28, 37, 120, 224, 255, 292, 901, 902; 510/247–253, 421, 422, 424, 427; 210/698, 764; 134/2–3, 22.1, 22.11, 22.14, 22.19, 36, 41–42

(56) References Cited

U.S. PATENT DOCUMENTS

| | | | |
|---|---|---|---|
| 3,411,983 A | | 11/1968 | Girard ............... 162/161 |
| 4,105,431 A | | 8/1978 | Lewis et al. ............ 71/67 |
| 4,438,258 A | * | 3/1984 | Graham ............... 528/361 |
| 4,547,517 A | * | 10/1985 | Kuhle et al. .......... 514/390 |
| 4,666,621 A | | 5/1987 | Clark et al. ............. 252/91 |
| 4,732,905 A | | 3/1988 | Donofrio et al. ....... 514/372 |
| 4,976,874 A | * | 12/1990 | Gannon et al. ........ 210/755 |
| 5,409,713 A | * | 4/1995 | Lokkesmoe et al. |
| 5,411,666 A | | 5/1995 | Hollis et al. ........... 210/632 |
| 5,444,078 A | | 8/1995 | Yu et al. .............. 514/372 |
| 5,512,186 A | | 4/1996 | Wright et al. ......... 210/764 |
| 5,593,599 A | | 1/1997 | Wright et al. ......... 210/764 |
| 5,603,941 A | | 2/1997 | Farina et al. .......... 424/405 |
| 5,607,597 A | | 3/1997 | Wright et al. ......... 210/755 |
| 5,670,055 A | * | 9/1997 | Yu et al. |
| 5,695,652 A | * | 12/1997 | Hernandez-Mena et al. |
| 5,736,058 A | * | 4/1998 | Wright et al. |
| 5,843,865 A | * | 12/1998 | Del Corral et al. ...... 504/160 |
| 5,935,920 A | * | 8/1999 | Geke et al. |
| 5,942,219 A | * | 8/1999 | Hendriks |

FOREIGN PATENT DOCUMENTS

GB   1560327   *   2/1980   .......... G02F/1/50

OTHER PUBLICATIONS

Costerton, J.W. et al, Bacterial Biofilms in Nature and Disease, Ann. Rev. Microbiol. 41:435–464 (1987).
Jass, J. et al., Microbial Biofilms in Industry: Wanted Dead or Alive?, Chem. and Ind. 17:682–685 (1997).
Lam, J.R. et al., Production of Mucoid Microcolonies by Pseudomonas Aeruginosa within Infected Lungs in Cystic Fibrosis.
Lamikana et al., The Antibacterial Activity of Non–Ionic Surface Active Agents, Microbios Letters 1:97–101 (1976).
Markwell, M.A. et al., A Modification of the Lowry Procedure to Simplify Protein Determination in Membrane and Liopoprotein Samples, Anal. Biochem. 87:206–210 (1978).
Marshal, K.C., Adsorption and Adhesion Processes in Microbial Growth at Interfaces, Adv. Colloid Interface Sci. 25:59–86 (1986).
McIlwaine D.B. et al., Determining the Biofilm Penetrating Ability of Various Biocides Using an Artificial Biofilm Matrix, Corrosion 97, Paper 400, 400/1–400/9, (1997).
Whitham, T.S. et al., Evaluation of a Model Biofilm for the Ranking of Biofilm Performance against Sulphate–Reducing Bacteria, J. Appl. Bacter. 75:529–535 (1993).
Whitekettle, Effects of Surface Active Chemicals on Microbial Adhesion, Journal of Industrial Microbiology, 7 (1991) 105–116.
Xu, P.S. et al., Transport Limitation of Chlorine Disinfection of Pseudomonas Aeruginosa Entrapped in Alginate Beads, Biotechnol. Bioeng. 45:93–100 (1995).

* cited by examiner

*Primary Examiner*—Robert J. Warden, Sr.
*Assistant Examiner*—Monzer R. Chorbaji
(74) *Attorney, Agent, or Firm*—Greenblum & Bernstein, P.L.C.

(57) ABSTRACT

Method for removing microbial biofilm from surfaces in contact with an aqueous system is disclosed, which comprises adding to the system a treatment comprising low foaming, ethoxylated anionic surfactant composed of alkyl substituted carboxylated acid or salt thereof and polyoxyethylene-polyoxypropylene block copolymer.

47 Claims, No Drawings

METHOD FOR REMOVING MICROBES FROM SURFACES

CROSS-REFERENCE TO RELATED APPLICATIONS

The present application is related to U.S. application Ser. No. 09/512,708, filed Feb. 25, 2000, for Method for Enhancing Biocidal Activity the disclosure of which is expressly incorporated by reference herein in its entirety.

BACKGROUND OF THE INVENTION

It is well established that bacteria attach to surfaces in virtually any non-sterile aquatic environment. Industrial efforts to prevent colonization or to clean fouled surfaces amount to costly expenditures in a number of industrial sectors. Often, such expenditures are made for cleaning programs that include the use of surfactants. Surfactants are regularly employed in water treatment programs as agents believed to play a role in the removal of organic masses from surfaces, in the enhancement of biocide efficacy or in the assistance in the water miscibility of various biocidal agents. Surfactants are also regularly used in the agrichemical business, particularly to enhance the action of herbicides. This is accomplished by using the surfactants to alter the surface behavior of the applied droplets, maximizing their interaction with the leaf surface.

There are numerous examples of surfactants which are able to inhibit the colonization of surfaces by inhibiting the overall growth of the organisms in the target environment. Most surfactants, regardless of class, inhibit surface colonization when used at concentrations high enough to impede bacterial growth. In the water treatment industry, the most well-known surfactants which impart a measure of colonization resistance to submerged surfaces are the cationic quaternary amine surfactants, which also function as biocides. However, even the relatively mild nonionic or anionic surfactants can exhibit toxic effects upon microbes, e.g., bacteria, algae or fungi; the concentration of nonionic surfactants necessary to mediate toxicity is typically substantially higher than for cationic surfactants, however.

Examples of nontoxic control of surface colonization typically require the use of high concentrations of surfactants not feasible in water treatment industries where thousands or millions of gallons of water would be treated.

The present invention relates to the use of surfactants which act by removing microbial biofilm from surfaces in contact with an aqueous system. These materials function to remove biofilm at concentrations below which toxicity has been observed for the tested organisms.

SUMMARY OF THE INVENTION

The present invention relates to methods for removing microbial biofilm on surfaces in contact with an aqueous system which comprises adding to the aqueous system an effective amount of a low foaming, ethoxylated anionic surfactant, the low foaming, ethoxylated anionic surfactant comprising (a) at least one of alkyl substituted carboxylated acid and alkyl substituted carboxylated acid salt, and (b) polyoxyethylene-polyoxypropylene block copolymer, to substantially remove microbial biofilm from the surfaces while preserving the viability of the microbes in the aqueous system, allowing for discharge of the microbes from the aqueous system.

The alkyl substituted carboxylated acid or salt can contain from 6 to 18 carbon atoms, preferably 6 to 12 carbon atoms, and even more preferably 6 to 9 carbon atoms. The alkyl groups can contain from 1 to 6 carbon atoms, preferably 1 to 3 carbon atoms, and even more preferably 1 carbon atom. Preferably, the alkyl substitution is on 3 and 5 carbon atoms of the carboxylic acid. Preferably, the alkyl substituted carboxylated acid or salt comprises at least one of 3,5,5 trimethyl hexanoic acid and salts thereof, 3,5,5 trimethyl octanoic acid and salts thereof, 3,7,7 trimethyl octanoic acid and salts thereof, 3,5,5 trimethyl decanoic acid and salts thereof, and 3,9,9 trimethyl decanoic acid and salts thereof.

Preferably, the alkyl substituted carboxylated acid or salt comprises alkyl substituted carboxylated acid salt, preferably a potassium or sodium salt.

The polyoxyethylene-polyoxypropylene block copolymer preferably has a mole ratio of about 1 to 1.6 moles of polyoxyethylene to 1 mole of polyoxypropylene, more preferably about 1.3 moles of polyoxyethylene to 1 mole of polyoxypropylene. The polyoxyethylene-polyoxypropylene block copolymer preferably has a molecular weight of about 3,000 to 6,600, more preferably about 4,000 to 5,000, and even more preferably about 4,500.

The low foaming, ethoxylated anionic surfactant preferably comprises about 35 to 60 wt % water, based upon total weight of the surfactant, preferably about 25 to 45 wt % of the at least one of alkyl substituted carboxylated acid and alkyl substituted carboxylated acid salt, and more preferably about 28 to 32 wt % of the at least one of alkyl substituted carboxylated acid and alkyl substituted carboxylated acid salt, and about 5 to 25 wt % of the polyoxyethylene-polyoxypropylene block copolymer, more preferably about 11 to 18 wt % of the polyoxyethylene-polyoxypropylene block copolymer.

The surfactant can include additional components such as at least one sequestrant, which preferably comprises at least one of polyepoxysuccinic acid and hydroxyethylidene diphosphonic acid.

At least about 5 ppm of the surfactant, more preferably at least about 10 ppm of the surfactant, can be added to the aqueous system, with preferred ranges being about 5 to 200 ppm, more preferably 10 to 50 ppm of the surfactant added to the aqueous system.

The microbes can comprise bacteria, fungi, algae and/or protozoa, including protozoan cysts.

The aqueous system can comprise at least one of cooling water systems (preferably recirculating and/or closed water systems), reverse osmosis systems, pulping and papermaking systems, air washer systems, pasteurizer systems, fire water safety systems, shower water systems, metalworking fluid systems, hydrocarbon storage systems, and aqueous mineral processing systems.

Preferably, the at least one of alkyl substituted carboxylated acid and alkyl substituted carboxylated acid salt comprises potassium or sodium salt of an alkyl substituted carboxylated acid having 6 to 12 carbon atoms and alkyl groups of 1 carbon atom, and the polyoxyethylene-polyoxypropylene block copolymer has a molecular weight of about 4,000 to 5,000 and a has a mole ratio of about 1 to 1.6 moles of polyoxyethylene to 1 mole of polyoxypropylene. More preferably, the potassium or sodium salt of an alkyl substituted carboxylated acid comprises a potassium or sodium salt of 3,5,5 trimethyl hexanoic acid.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

Unless otherwise stated, all percentages, parts, ratios, etc., are by weight. Also, all percent measurements in this application, unless otherwise stated, are measured by weight based upon 100% of a given sample weight. Thus, for example, 30% represents 30 weight parts out of every 100 weight parts of the sample.

Unless otherwise stated, a reference to a compound or component includes the compound or component by itself, as well as in combination with other compounds or components, such as mixtures of compounds.

Further, when an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed.

The dispersant of the present invention removes and/or reduces microbial slime from surfaces in contact with aqueous systems better than that caused by water alone. This "environmental friendly" control methodology removes biofilm, but does not negatively impact non-target organisms which may be encountered in waste treatment systems or waters receiving the industrial discharge. Further, the chemicals utilized in the dispersant are preferably biodegradable. Moreover, the dispersant according to the present invention includes a combination of alkyl substituted carboxylated acid salt and polyoxyethylene-polyoxypropylene block copolymer that when agitated, such as in cooling towers, will not form excessive amounts of foam, which would be unacceptable for use in various aqueous systems.

The present invention relates to compositions and methods for removing microbial biofilm on surfaces in contact with an aqueous system which comprises adding to the aqueous system an effective amount of a dispersant comprising low foaming, ethoxylated anionic surfactant, said low foaming, ethoxylated anionic surfactant comprising (a) at least one of alkyl substituted carboxylated acid and alkyl substituted carboxylated acid salt, and (b) polyoxyethylene-polyoxypropylene block copolymer, to substantially remove microbial biofilm from the surfaces while preserving the viability of the microbes in the aqueous system, allowing for discharge of the microbes from the aqueous system. Removing microbial biofilm on surface includes a reduction of the biofilm from the surface and/or the substantial removal of the biofilm and/or complete removal of the biofilm from the surface.

The alkyl substituted carboxylated acid or salt thereof can include, but is not limited to, acids and/or salts containing from about 6 to 18 carbon atoms, more preferably from about 6 to 12 carbon atoms, and most preferably from about 6 to 9 carbon atoms. Moreover, the alkyl groups can comprise alkyl groups having from about 1 to 6 carbon atoms, more preferably from about 1 to 3 carbon atoms, and most preferably 1 carbon atom. Preferably, the alkyl substituted carboxylated acid or salt comprises up to about 7 alkyl groups, and preferably contains 3 alkyl groups. Preferably, the acid comprises hexanoic, octanoic and/or decanoic acid, with from 1 to 3 alkyl groups on the various carbons of the acid, which are preferably methyl groups. Moreover, preferably the alkyl substitution is on the 3 and 5 carbons, preferably of hexanoic acid. Particularly preferred alkyl substituted carboxylated acid or salt thereof comprises hexanoic acid, with the alkyl substitution being on the 3 and 5 carbons, preferably one alkyl group on the 3 carbon and two alkyl groups of the 5 carbon, and preferably each of the three alkyl groups are methyl. Thus, a particularly preferred alkyl substituted carboxylated acid or salt thereof comprises 3, 5, 5 hexanoic acid or salt thereof. Preferably, the alkyl substituted carboxylated acid and/or salt thereof comprises the salt. The salt form can include any cation that helps dissolve the carboxylic acid into solution, and preferably comprises potassium or sodium as the cation. For example, the acid can be formed into the salt by reaction with potassium hydroxide or sodium hydroxide. Examples of alkyl substituted carboxylated acid and salts according to the present invention include, but are not limited to, 3,5,5 trimethyl hexanoic acid and salts thereof, preferably sodium or potassium salts thereof, 3,5,5 trimethyl octanoic acid and salts thereof, 3,7,7 trimethyl octanoic acid and salts thereof, 3,5,5 trimethyl decanoic acid and salts thereof, and 3,9,9 trimethyl decanoic acid and salts thereof.

The block copolymer comprises polyoxyethylene (EO)-polyoxypropylene (PO), which for the sake of convenience will also be referred to herein as EO/PO block copolymer. The EO/PO block copolymer can comprise any EO/PO that maintains low foaming and/or reduces foaming of the alkyl substituted carboxylated acid or salt. The EO/PO mole ratio preferably ranges from about 1 to 1.6 moles EO to 1 mole PO, with a particularly preferred mole ratio being about 1.3 moles EO to 1 mole PO.

The molecular weight range of the EO/PO is preferably about 3,000 to 6,600, most preferably about 4,000 to 5,000, with a particularly preferred value being about 4,500. Thus, a particularly preferred EO/PO block copolymer comprises EO/PO having 1.3 moles EO to 1 mole PO, and a molecular weight of about 4,500.

Examples of EO/PO block copolymers according to the present invention include, but are not limited to, the Plutonic P series available from BASF (Mount Olive, N.J.), and examples thereof include P65, P68, P84, P85, P104 and P105.

An especially useful material for forming the dispersant of the present invention is Mona NF 10, available from Uniqema, Paterson, N.J. (formerly Mona Industries, Inc.), which includes therein alkyl substituted carboxylated acid salt and EO/PO compound according to the present invention.

Still further, a particularly preferred low foaming, ethoxylated anionic surfactant according to the present invention is composed of the potassium salt of 3,5,5 trimethyl hexanoic acid and EO/PO block copolymer having a molecular weight of about 4,500, such as P85 available from BASF.

The dispersant preferably comprises about 35 to 70 wt % water, based on the total weight of the dispersant. The amount of the alkyl substituted carboxylated acid or salt in the dispersant is preferably from about 25 to 45 wt %, more preferably from about 28 to 32 wt %, based on the total weight of the dispersant. Moreover, the amount of the EO/PO block copolymer in the dispersant is preferably from about 5 to 25 wt %, more preferably from about 11 to 18 wt %, based on the total weight of the dispersant.

Materials in addition to the alkyl substituted carboxylated acid salt, and the EO/PO block copolymer can be included in the dispersant according to the present invention. For example, additives such as sequestrants such as polyepoxysuccinic acid, hydroxyethylidene diphosphonic acid, citric acid and/or ethylenediamine tetraacetic acid (EDTA) can be included in the dispersant according to the present invention.

The dispersant, by itself, or including sequestrants such as polyepoxysuccinic acid or hydroxyethylidene diphosphonic acid, is able to remove biofilms from surfaces in contact with aqueous systems, while not negatively impacting non-target organisms which may be encountered in the aqueous system.

The dispersant according to the present invention is preferably included in the aqueous system at a concentration of at least about 5 parts per million (ppm), more preferably at least about 10 ppm, with preferred ranges being about 5 to 200 ppm, more preferably about 10 to 100 ppm, more preferably about 25 to 100 ppm.

The dispersant according to the present invention can be utilized in a variety of aqueous systems, e.g., open recirculating cooling water systems, closed cooling systems, reverse osmosis systems, pulping or papermaking systems, air washer systems, pasteurizer systems, once-through cooling reverse osmosis systems, fire water safety systems, shower water systems, metalworking fluid systems, hydrocarbon storage systems, and aqueous mineral processing systems.

The invention will now be described with respect to certain examples which are merely representative of the invention and should not be construed as limiting thereof.

EXAMPLES

The invention is illustrated in the following non-limiting examples, which are provided for the purpose of representation, and are not to be construed as limiting the scope of the invention. All parts and percentages in the examples are by weight unless indicated otherwise.

In order to demonstrate efficacy of the present invention, a method was developed which allowed for the screening of dispersant ability to remove a bacterial biofilm. This method involved the colonization of commercially available galvanized steel coupons by bacteria, and their removal in the presence/absence of dispersants. The number of bacteria on a set of coupons was then determined by standard methods.

The bacterial species *Pseudomonas aeruginosa*, (*P. aeruginosa*) was the organism chosen for these studies because this species has frequently been demonstrated to be among the primary colonizers of submerged surfaces. These organisms are also nearly ubiquitous in natural aquatic environments and could, therefore, be expected to be found in process water streams in a variety of industries; the strain used was a cooling tower isolate.

In experiments, biofilm contaminated galvanized steel coupons were made by contaminating the galvanized steel coupons with *P. aeruginosa* for 10 to 11 days at a temperature of 22–24° C. via semi-batch and/or continuous procedure. Media was constantly mixed, simulating flow conditions. At day 10 or 11, sufficient biofilm was found on the coupons for testing.

Biofilm contaminated coupons were submerged in 100 ppm surfactant (Mona NF- 10, obtained from Uniqema, Paterson, N.J. (formerly Mona Industries, Inc.) with and without sequestrant (polyepoxysuccinic acid obtained from BetzDearborn Inc., Trevose, Pa.) for 20 hours. The temperature of treatment was 25±3° C. The solution was slowly mixed to simulate flow conditions. The biofilm/slime remaining on the coupon after the treatment period was determined using a standard protein determination procedure. Results from coupons treated with the surfactant were compared to those treated with water alone. It was found that the surfactant treatment, with and without sequestrant, was able to consistently remove more biofilm from surfaces than just water. Removal with surfactant alone was about 40–54%, and with surfactant/sequestrants, about 65% (Table 1).

TABLE 1

| Example No. | Treatment: | ppm product | Protein μg/mL on surface | Percent Decrease from water control |
|---|---|---|---|---|
| 1 | Water | — | 257 | — |
| 2 | Mona NF-10 | 100 | 137 | 47 |
| 3 | Water | — | 198 | — |
| 4 | Mona NF-10 | 100 | 119 | 40 |
| 5 | Water | — | 168 | — |
| 6 | Polyepoxysuccinic acid | 10 | 122 | 27 |
| 7 | Mona NF-10 | 100 | 110 | 40 |
| 8 | Mona NF-10 Polyepoxysuccinic acid | 100 10 | 59 | 65 |
| 9 | Water | — | 298 | — |
| 10 | Mona NF-10 | 100 | 137 | 54 |
| 11 | Mona NF-10 Polyepoxysuccinic acid | 100 10 | 116 | 61 |

In further experiments, bacteria were incorporated into alginate which was formed into beads or layered on metal coupons. Beads, or layers were exposed to surfactant (Mona NF-10 obtained from Uniqema, Paterson, N.J. (formerly Mona Industries, Inc.) with and without sequestrant (polyepoxysuccinic acid obtained from BetzDearborn Inc., Trevose, Pa.), Still further, Dispersant A is prepared by mixing 38 wt % 3,5,5 trimethyl hexanoic acid (obtained from BetzDearborn Inc., Trevose, Pa.) and 12 wt % P85 (obtained from BASF (Mount Olive, N.J.) with sufficient KOH to get the 3,5,5 trimethyl hexanoic acid into solution. At the end of the treatment, the alginate was dissolved, releasing bacteria which were monitored by determining viable numbers of bacteria and microbial ATP levels. As shown in Table 2 below, the surfactant with and without sequestrants did not adversely affect bacteria in alginate.

TABLE 2

| Example No. | Treatment: Product (ppm) | CFU/ml | Percent Reduction | M-ATP (RLU) | Percent Reduction |
|---|---|---|---|---|---|
| 12 | Control (Water) | 1.32E8 | — | 67481 | — |
| 13 | Mona NF-10 (100 ppm) | 1.43E8 | 0% | 66780 | <5% |
| 14 | Mona NF-10 (100 ppm) Polyepoxysuccinic acid (10 ppm) | 1.37E8 | 0% | 65262 | <5% |
| 15 | Control (Water) | 1.9E8 | — | — | — |
| 16 | Dispersant A (50 ppm) | 2.4E8 | 0% | — | — |

As shown above, the bacterial numbers and ATP values of the sample treated with surfactant were comparable with control samples (untreated). This demonstrates the "environmentally friendly" nature of the particular treatment.

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. A method for removing microbial biofilm on surfaces in contact with an aqueous system which comprises adding to the aqueous system an effective amount of an ethoxylated anionic surfactant, said ethoxylated anionic surfactant comprising (a) at least one of alkyl substituted carboxylated acid and alkyl substituted carboxylated acid salt, and (b) polyoxyethylene-polyoxypropylene block copolymer, to remove microbial biofilm from the surfaces while preserving the viability of the microbes in the aqueous system, allowing for discharge of the microbes from the aqueous system.

2. The method according to claim 1, wherein said alkyl substituted carboxylated acid or salt contains from 6 to 18 carbon atoms.

3. The method according to claim 2, wherein said alkyl substituted carboxylated acid or salt comprises alkyl groups having from 1 to 6 carbon atoms.

4. The method according to claim 3, wherein said alkyl substituted carboxylated acid or salt comprises alkyl groups having from 1 to 3 carbon atoms.

5. The method according to claim 4, wherein said alkyl substituted carboxylated acid or salt comprises alkyl groups having 1 carbon atom.

6. The method according to claim 5, wherein alkyl substitution is on 3 and 5 carbon atoms of the carboxylic acid.

7. The method according to claim 2, wherein said alkyl substituted carboxylated acid or salt contains from 6 to 12 carbon atoms.

8. The method according to claim 7, wherein said alkyl substituted carboxylated acid or salt comprises alkyl groups having from 1 to 6 carbon atoms.

9. The method according to claim 8, wherein said alkyl substituted carboxylated acid or salt comprises alkyl groups having from 1 to 3 carbon atoms.

10. The method according to claim 9, wherein said alkyl substituted carboxylated acid or salt comprises alkyl groups having 1 carbon atom.

11. The method according to claim 10, wherein alkyl substitution is on 3 and 5 carbon atoms of the carboxylic acid.

12. The method according to claim 7, wherein said alkyl substituted carboxylated acid or salt contains from 6 to 9 carbon atoms.

13. The method according to claim 12, wherein said alkyl substituted carboxylated acid or salt comprises alkyl groups having from 1 to 6 carbon atoms.

14. The method according to claim 13, wherein said alkyl substituted carboxylated acid or salt comprises alkyl groups having from 1 to 3 carbon atoms.

15. The method according to claim 14, wherein said alkyl substituted carboxylated acid or salt comprises alkyl groups having 1 carbon atom.

16. The method according to claim 15, wherein alkyl substitution is on 3 and 5 carbon atoms of the carboxylic acid.

17. The method according to claim 1, wherein the alkyl substituted carboxylated acid or salt comprises alkyl substituted carboxylated acid salt.

18. The method according to claim 17, wherein the alkyl substituted carboxylated acid salt comprises potassium or sodium salt.

19. The method according to claim 1, wherein the alkyl substituted carboxylated acid or salt comprises at least one of 3,5,5 trimethyl hexanoic acid and salts thereof, 3,5,5 trimethyl octanoic acid and salts thereof, 3,7,7 trimethyl octanoic acid and salts thereof, 3,5,5 trimethyl decanoic acid and salts thereof, and 3,9,9 trimethyl decanoic acid and salts thereof.

20. The method according to claim 1, wherein the polyoxyethylene-polyoxypropylene block copolymer has a mole ratio of about 1 to 1.6 moles of polyoxyethylene to 1 mole of polyoxypropylene.

21. The method according to claim 20, wherein the polyoxyethylene-polyoxypropylene block copolymer has a molecular weight of about 3,000 to 6,600.

22. The method according to claim 21, wherein the polyoxyethylene-polyoxypropylene block copolymer has a molecular weight of about 4,000 to 5,000.

23. The method according to claim 22, wherein the polyoxyethylene-polyoxypropylene block copolymer has a molecular weight of about 4,500.

24. The method according to claim 20, wherein the polyoxyethylene-polyoxypropylene block copolymer has a mole ratio of about 1.3 moles of polyoxyethylene to 1 mole of polyoxypropylene.

25. The method according to claim 24, wherein the polyoxypropylene-polyoxyethylene block copolymer has a molecular weight of about 3,000 to 6,600.

26. The method according to claim 25, wherein the polyoxyethylene-polyoxypropylene block copolymer has a molecular weight of about 4,000 to 5,000.

27. The method according to claim 26, wherein the polyoxyethylene-polyoxypropylene block copolymer has a molecular weight of about 4,500.

28. The method according to claim 1, wherein the ethoxylated anionic surfactant comprises water about 35 to 70 wt % water, based upon total weight of the surfactant.

29. The method according to claim 28, wherein the ethoxylated anionic surfactant comprises about 25 to 45 wt % of the at least one of alkyl substituted carboxylated acid and alkyl substituted carboxylated acid salt, based upon total weight of the surfactant.

30. The method according to claim 29, wherein the ethoxylated anionic surfactant comprises about 28 to 32 wt % of the at least one of alkyl substituted carboxylated acid and alkyl substituted carboxylated acid salt, based upon total weight of the surfactant.

31. The method according to claim 29, wherein the ethoxylated anionic surfactant comprises about 5 to 25 wt % of the polyoxyethylene-polyoxypropylene block copolymer, based upon total weight of the surfactant.

32. The method according to claim 29, wherein the ethoxylated anionic surfactant comprises about 11 to 18 wt % of the polyoxyethylene-polyoxypropylene block copolymer, based upon total weight of the surfactant.

33. The method according to claim 1, wherein the surfactant additionally includes at least one sequestrant.

34. The method according to claim 33, where the at least one sequestrant comprises at least one of polyepoxysuccinic acid and hydroxyethylidene diphosphonic acid.

35. The method according to claim 1, wherein at least about 10 ppm of the surfactant is added to the aqueous system.

36. The method according to claim 1, wherein about 5 to 200 ppm of the surfactant is added to the aqueous system.

37. The method according to claim 36, wherein about 10 to 100 ppm of the surfactant is added to the aqueous system.

38. The method according to claim 1, wherein said microbes comprise bacteria.

39. The method according to claim 1, wherein said microbes comprise at least one of fungi, algae and protozoa.

40. The method according to claim 39, wherein said microbes comprise fungi.

41. The method according to claim 39, wherein said microbes comprise algae.

42. The method according to claim 1, wherein said aqueous system comprises at least one of cooling water systems, reverse osmosis systems, pulping and papermaking systems, air washer systems, pasteurizer systems, fire water safety systems, shower water systems, metalworking fluid systems, hydrocarbon storage systems, and aqueous mineral processing systems.

43. The method according to claim 42, wherein said aqueous system comprises a cooling water system.

44. The method according to claim 43, wherein the cooling water system comprises recirculating and/or closed water systems.

45. The method according to claim 42, wherein the aqueous system comprises a pulping or papermaking system.

46. The method according to claim 1, wherein the at least one of alkyl substituted carboxylated acid and alkyl substituted carboxylated acid salt comprises a potassium or sodium salt of an alkyl substituted carboxylated acid having 6 to 12 carbon atoms and alkyl groups of 1 carbon atom, and the polyoxyethylene-polyoxypropylene block copolymer has a molecular weight of about 4,000 to 5,000 and has a mole ratio of about 1 to 1.6 moles of polyoxyethylene to 1 mole of polyoxypropylene.

47. The method according to claim 46, wherein the potassium or sodium salt of an alkyl substituted carboxylated acid comprises a potassium or sodium salt of 3,5,5 trimethyl hexanoic acid.

* * * * *